United States Patent [19]

Felding

[11] Patent Number: 5,173,125
[45] Date of Patent: Dec. 22, 1992

[54] SYSTEM FOR CONTROLLING MEDICAL TREATMENTS SUCH AS DIALYSIS

[75] Inventor: Anders Felding, Malmö, Sweden

[73] Assignee: Gambro AB, Sweden

[21] Appl. No.: 702,622

[22] Filed: May 17, 1991

[30] Foreign Application Priority Data

May 25, 1990 [SE] Sweden ................ 9001890

[51] Int. Cl.$^5$ ............... B08B 3/00; B08B 9/00
[52] U.S. Cl. .................. 134/22.11; 134/18; 134/22.12; 134/96.1
[58] Field of Search ............ 134/18, 22.12, 22.11, 134/96, 98, 103

[56] References Cited

U.S. PATENT DOCUMENTS

| | | | |
|---|---|---|---|
| 3,753,493 | 8/1973 | Mellor | 210/321.74 |
| 3,871,913 | 3/1975 | Shaldon | 134/22.11 |
| 4,122,010 | 10/1978 | Riede et al. | 210/90 |
| 4,728,496 | 3/1988 | Petersen et al. | 210/321.69 |
| 4,784,495 | 11/1988 | Jonsson et al. | 137/88 |

*Primary Examiner*—Theodore Morris
*Assistant Examiner*—Zeinab El-Arini
*Attorney, Agent, or Firm*—Lerner, David, Littenberg, Krumholz & Mentlik

[57] ABSTRACT

Systems for controlling medical treatment procedures such a dialysis are disclosed, including a fluid flow inlet for feeding a treatment fluid to a medical treatment device such as a dialyzer, a fluid flow outflow path for withdrawing contaminated fluid from the medical device, a diversion channel for diverting a fluid flowing in the fluid flow inlet path from a point in that path upstream of the medical treatment device in order to bypass the medical treatment device, and a solvent supply, a cartridge containing a cleaning composition, and a connector for connecting the cartridge to the solvent supply and to the fluid flow inlet path, so that solvent can be mixed with the cleaning composition in the cartridge, and the mixture can be passed through the fluid of inlet path in order to clean the fluid flow in the path when the diversion channel diverts the fluid past the medical treatment device. Methods for controlling the flow of treatment fluids through medical treatment devices are also disclosed.

40 Claims, 2 Drawing Sheets

SYSTEM FOR CONTROLLING MEDICAL TREATMENTS SUCH AS DIALYSIS

FIELD OF THE INVENTION

The present invention relates to systems for controlling medical treatments. More particularly, the present invention relates to systems for controlling medical treatments such as dialysis, which preferably employ heated treatment fluids.

Still more particularly, the present invention relates to systems for controlling the flow of fluids through medical treatment devices, and means for connecting these systems to such devices, such as dialyzers, so that disinfection and/or sterilization and/or other cleaning of the system can be effected by using a liquid flowing through the same path as the treatment fluid itself, and in which the liquid is diverted past the treatment device The present invention also relates to methods for controlling such medical treatments.

More particularly, the present invention relates to systems intended for the preparation of dialysis fluids in connection with hemodialysis, but which with modification can be used for the preparation of replacement fluids in connection with hemofiltration and/or hemodiafiltration.

As can be seen by one skilled in this art, the systems of the present invention can also be used in connection with other treatment methods in which the treatment fluid is used or produced, such as wound rinsing fluids.

BACKGROUND OF THE INVENTION

Treatment fluids based on bicarbonate were originally used in dialysis systems. When these systems, and the monitors for same, were later automated, however, difficulties such as precipitation arose from the use of these bicarbonates. Other treatment fluids were therefore used instead, such as fluids based on acetates. Recently, however, bicarbonate-based liquids have again found favor, and at the same time, the problems which were previously thought to be insurmountable have, in the main, been overcome. However, certain problems still remain with respect to precipitation. Also, the systems in current use must be cleansed at regular intervals. This has been achieved heretofore by rinsing these systems with the aid of a cleansing liquid, such as citric acid.

U.S. Pat. No. 4,728,496 describes a system for disinfection and/or sterilization of systems, such as dialysis monitors. According to this patent, the fluid used for the treatment is recirculated within the part of the system which precedes the dialyzer. As is explained below, this system can, after certain additions, also be used for application of the present invention.

U.S. Pat. No. 4,784,495 describes another system for the control of medical treatments, such as dialysis, in which the treatment fluid to be employed is prepared from a powder-based concentrate, such as sodium bicarbonate. Even in this system, the present invention can also be advantageously applied.

It is therefore an object of the present invention to provide a simple method for cleaning systems of the above-mentioned type.

SUMMARY OF THE INVENTION

In accordance with the present invention, these and other objects have been accomplished by providing apparatus for controlling the flow of a treatment fluid through a medical treatment device which subjects the treatment fluid to contamination, the apparatus including a fluid flow inlet path for feeding the treatment fluid to the medical treatment device, a fluid flow outflow path for withdrawing the contaminated fluid from the medical treatment device, diversion means for diverting a fluid flowing in the fluid flow inlet path from a point in the fluid flow inlet path upstream of the medical treatment device so as to bypass the medical treatment device, and cleaning means for providing a cleaning fluid in place of the treatment fluid for cleaning the apparatus, the cleaning means including solvent supply means, cartridge means containing a cleaning composition, and connection means for connecting the cartridge means to the solvent supply means and to the fluid flow inlet path whereby the solvent can be mixed with the cleaning composition in the cartridge means and the mixture can be passed through the fluid flow inlet path in order to clean the fluid flow inlet path when the diversion means diverts the fluid past the medical treatment device.

The apparatus of the present invention is thus characterized by means for connecting a cartridge or other vessel to a conduit in the system in which the cartridge or other vessel contains a soluble concentrate in liquid or powder form, preferably in the form of a powder, which at least aids in the cleaning process, as well as by means for supplying water or another such solvent to the conduit to flow through and dissolve the concentrate therein. The system of the present invention preferably includes means for recirculating at least a portion of the fluid within at least a portion of the apparatus. Accordingly, this recirculation is suitably arranged to be effected by utilizing a return conduit from a location downstream in the system to a location at the upstream portion of the system in a manner described, for example, in above-mentioned U.S. Pat. No. 4,728,496.

In accordance with a preferred embodiment of the apparatus of the present invention, the apparatus includes heating means for controlling the supply of heat to the fluid at a predetermined heating location in the fluid flow inlet path.

In accordance with another embodiment of the apparatus of the present invention, the diversion means includes recirculation means for recirculating at least a portion of the fluid from a point in the fluid flow inlet path upstream of the medical treatment device to a point further upstream in the fluid flow inlet path. Preferably, such recirculation is effected from this bypass arrangement; that is, within the portion of the system which normally contains one of the treatment device's unaffected treatment fluids. Preferably, no recirculation occurs in the part of the system which normally has treatment fluid flowing therethrough which has been effected by and thus possibly contaminated by the treatment device.

In accordance with a preferred embodiment of the apparatus of the present invention, the recirculation means is adapted to recirculate the entire amount of the fluid from the point in the fluid flow inlet path upstream of the medical treatment device to the point further upstream in the fluid flow inlet path.

In accordance with another embodiment of the apparatus of the present invention, the apparatus includes heating means for controlling the supply of heat to the fluid at a predetermined heating location in the fluid flow inlet path, and the heating means is adapted to increase the temperature of the fluid to a predetermined temperature such that the temperature of the fluid in the recirculation means does not drop substantially below that predetermined temperature, and the temperature of the fluid in the fluid flow outflow path is permitted to decrease to a temperature below the predetermined temperature. Preferably, the predetermined temperature is 90° C. and the temperature below the predetermined temperature is about 80° C. In this manner, cleaning of the most important parts of the system, i.e., the parts which precede the medical treatment device or dialyzer, is ensured, while, at the same time, satisfactory cleaning of the subsequent parts in the system is also achieved. Considerably lower temperatures can, of course, also be selected, particularly if cleaning alone is desired. The temperature is naturally dependent upon which cleaning material is being utilized.

In accordance with another embodiment of the apparatus of the present invention, pressure control means are provided for monitoring the pressure in the apparatus, whereby the cleaning means can clean the fluid flow inlet path substantially at atmospheric pressure. The cleaning process is thus preferably arranged to take place at substantially normal atmospheric pressure, and in this way dimensioning of the system is made easier and less expensive.

In accordance with another embodiment of the apparatus of the present invention, the diversion means includes bypass means for bypassing at least a portion of the fluid from the point in the fluid flow inlet path upstream of the medical treatment device to the fluid flow outflow path.

In accordance with a preferred embodiment of the apparatus of the present invention, the recirculation means is adapted to recirculate a substantial flow of the fluid, and the bypass means is adapted to bypass a reduced flow of the fluid, the reduced flow corresponding to only a portion of the substantial flow. In this manner, effective cleaning is achieved, since substantially maximum flow takes place in the recirculation circuit, while the flow in the remainder of the system is maintained at a fraction, such as about one-fifth thereof.

In accordance with another embodiment of the apparatus of the present invention, the recirculation means includes throttle means. Preferably, throttle control means are also provided for opening or bypassing the throttle means during cleaning so as to reduce the flow resistance in the fluid flow inlet path. In this manner, it is possible to guarantee that all parts of the system are cleansed.

In accordance with another embodiment of the apparatus of the present invention, the cartridge means comprises a plurality of cartridge means. Thus, if the treatment fluid, preferably heated treatment fluid, is arranged to be prepared by connecting a cartridge or other such vessel including a compound, such as a powder-based concentrate, therein, and the means for connecting the various cartridges can be identical. Such is the case, for example, where the present invention is applied to a system according to abovereferenced U.S. Pat. No. 4,784,495. The cartridge containing cleaning concentrate can thus be connected during cleaning instead of the normally connected cartridge containing treatment concentrate during normal use. The system and its control means is thus programmed in a manner such that treatment and cleaning cannot be confused.

The present invention also comprises a cartridge or other vessel which is intended to be used in the above-described apparatus. These cartridges are characterized in that they contain precisely the desired quantity of concentrate necessary for cleaning with regard to the normal fluid volume in the system and for selected cleaning temperatures. Furthermore, in order to ensure that the cleaning concentrate is not contaminated or in any way contacted with undesirable substances, the cartridge is produced completely sealed and is provided with penetrable membranes at its inlet and outlets. These cartridges preferably contain concentrates such as citric acid, peracetic acid, oxalic acid, sodium hydroxide, sodium hypochloride, sodium carbonate or suitable combinations thereof, but citric acid is preferred. In practice, it has thus been shown to be useful to use citric acid in the crystalline form. If a finer powder is used, then a risk of clogging the cartridge can arise.

According to the present invention, a method has also been devised for controlling the flow of a treatment fluid through a medical treatment device which subjects that treatment fluid to contamination, the method including feeding the treatment fluid through a fluid flow inlet path to the medical treatment device, withdrawing the contaminated fluid through a fluid flow outflow path from the medical treatment device, diverting a fluid flowing in a fluid flow inlet path from a point upstream of the medical treatment device through a diversion path so as to bypass the medical treatment device, providing a cleaning fluid in place of the treatment fluid for cleaning the fluid flow inlet path and the diversion path by providing a solvent for connecting a cartridge containing a cleaning composition to the solvent and the fluid flow inlet path, whereby the solvent is mixed with the cleaning composition in the cartridge, and passing the mixture through the fluid flow inlet path so as to clean the fluid flow inlet path when the cleaning fluid is diverted through the diversion path.

BRIEF DESCRIPTION OF THE DRAWINGS

The following detailed description can be more fully appreciated with reference to the following drawings in which.

DETAILED DESCRIPTION

Figure 1:
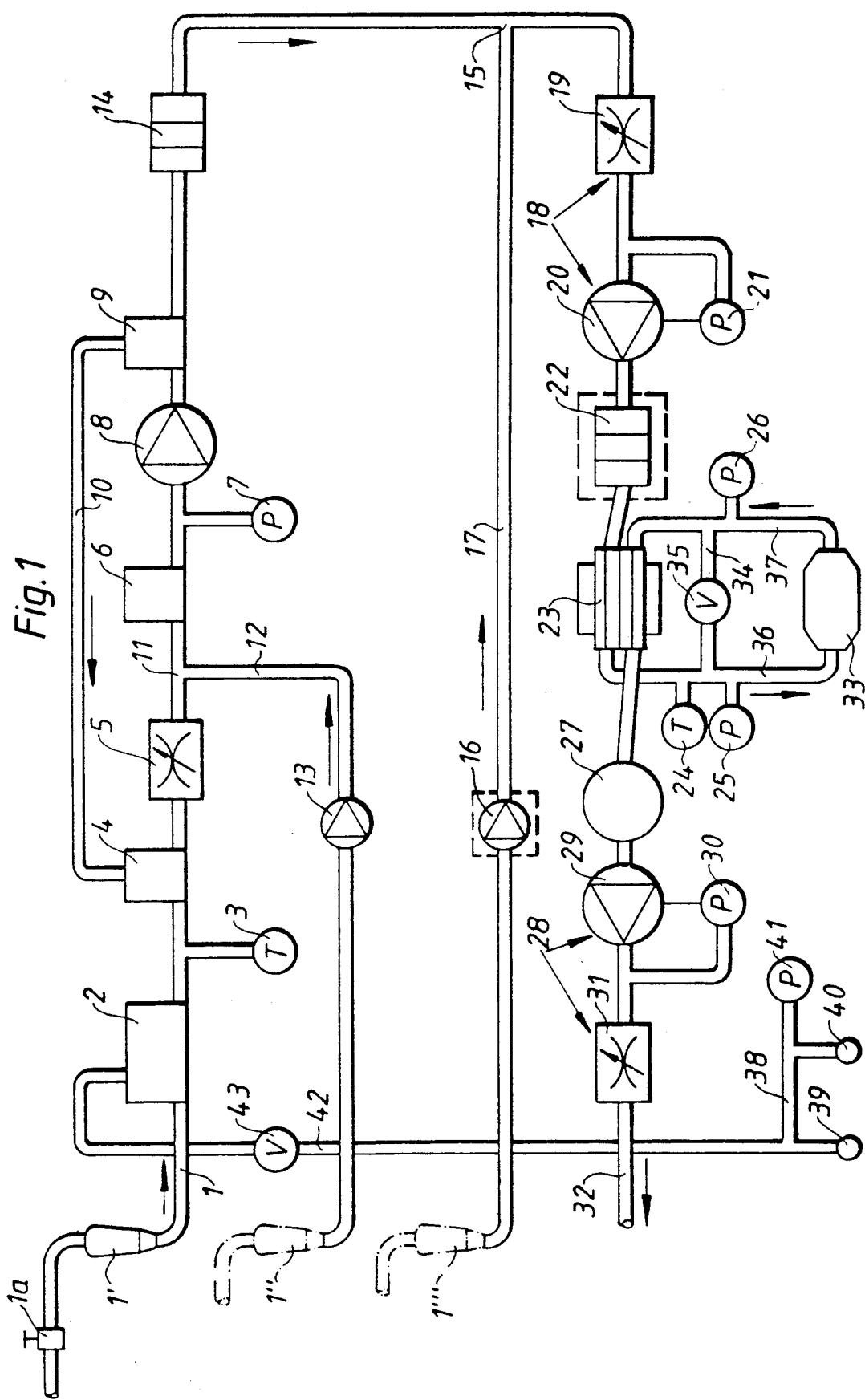
FIG. 1 is a schematic representation of a system designed in accordance with the present invention.
Figure 2:
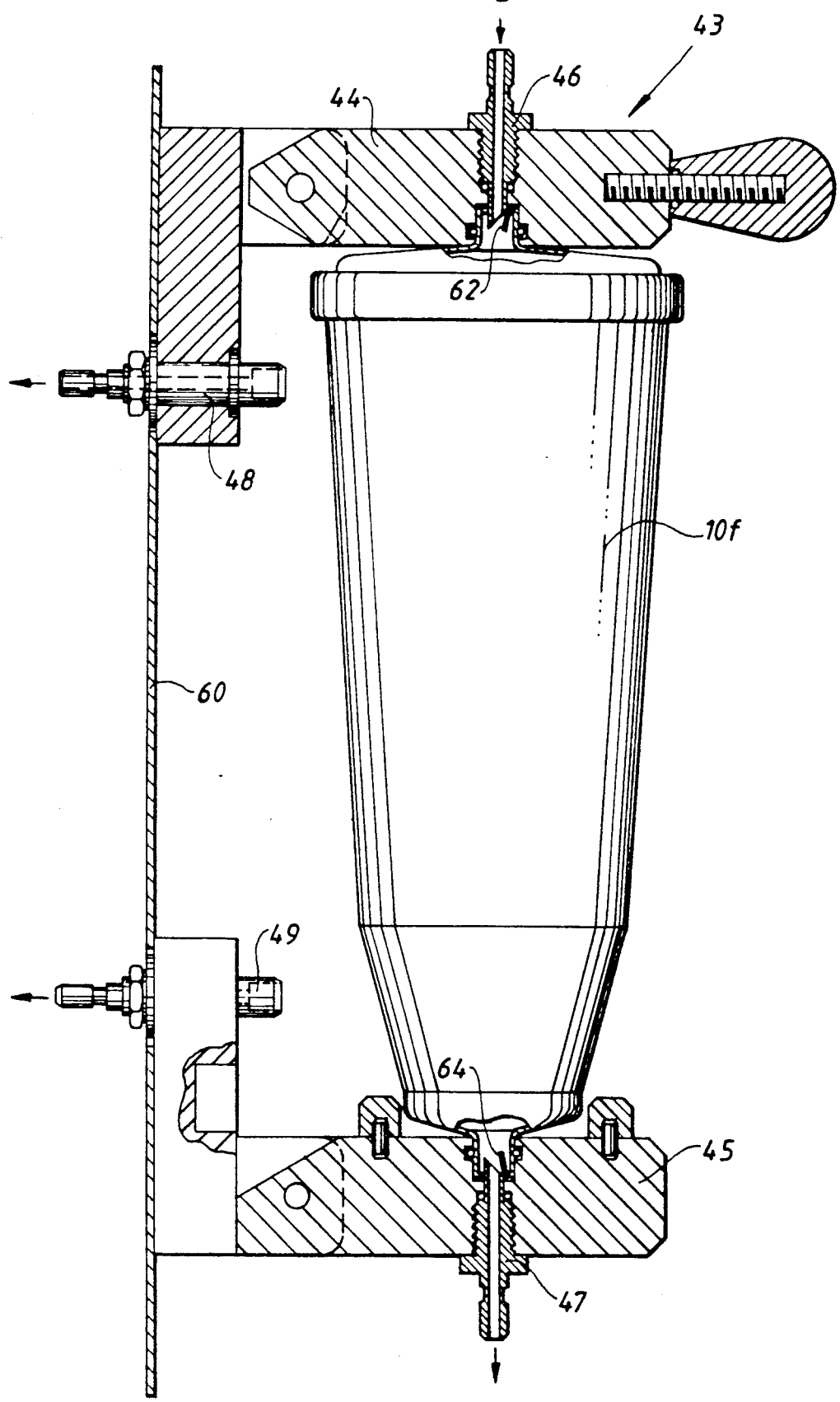
FIG. 2 is a side, partially sectional view of apparatus for connecting a cartridge or other vessel intended to contain cleaning concentrate to the system shown in FIG. 1.

Referring to the aforementioned Figures, in which like numerals refer to like portions thereof, referring initially to FIG. 1, in using that system water is supplied through an inlet $1a$ by means of a water conduit 1 to a heating device 2, where it is heated. In the illustrated schematic diagram, three possible connection positions, designated $1'$, $1''$, and $1'''$, are shown for connecting the above-discussed cartridge or other vessel containing a cleansing concentrate to the system. A preferred such cartridge is also shown in FIG. 2, by reference numeral $10f$, together with means for its connection to the system.

The water is then passed from the heating device 2, with or without cleansing concentrate, past a temperature measuring device 3, a return vessel 4, a throttle 5, a bubble-expansion chamber 6, a pressure measuring device 7 and a pump 8, to a ventilating chamber 9. A return conduit 10 leads from the ventilator chamber 9 back to the return vessel 4, for returning separated air or other gases, together with a small quantity of fluid. Instead, a return line to the heating vessel 2 could be provided, but this would require the use of specific resistant material, since dialysis concentrate is normally supplied to the point 11 through conduit 12, with the assistance of pump 13. This part of the system corresponds in general with the systems described, for example, in U.S. Pat. Nos. 4,158,034 and 4,293,409, both of which are incorporated herein by reference thereto. The function of the expansion chamber 6 is described in more detail in U.S. Pat. No. 4,536,201, which is also incorporated herein by reference thereto. Fluid is then led from the ventilating chamber 9, through conductivity measuring cell 14, to a further mixing point 15, where any additional concentrate is supplied with the assistance of pump 16, and a conduit 17. This is based upon the assumption that a two-component-based dialysis concentrate is to be used, such as the type which is described in European Patent No. B-0,022,922. Dialysis fluid is led from the mixing point 15 through a first constant flow device 18, which comprises a throttle 19, a pump 20 and a pressure measuring device 21.

The pressure measured by the pressure measuring device 21 is thus used for controlling the pump 20, so that a desired constant flow is achieved thereby. Downstream of the pump 20, the fluid flow is then led through a conductivity measuring device 22 and ultra-filtration control 23, past a temperature measurer 24, and a pressure measurer 25, to the dialyzer 33. From the dialyzer 33, the flow is then normally led past a pressure measurer 26, the ultra-filtration control 23, and a blood detector 27, to a further constant flow device 28, which comprises a pump 29, a pressure measurer 30 and a throttle device 31. The dialysate is finally led to an outlet 32.

The construction and function of the ultra-filtration control 23 is described in more detail in British Patent No. B-2,003,274 and European Patent No. B-0,106,940. Reference numeral 33 denotes the dialyzer which is connectable to the system according to this invention, to whose blood-side the patient is connected. This latter connection is, however, not shown in FIG. 1.

The dialyzer 33 can be bypassed in two ways. This can either occur with the aid of bypass conduit 34, with valve 35, which can be opened, for example, if the temperature or the conductivity exceeds or falls below predetermined levels. At the same time, when this occurs, the flow to the dialyzer is interrupted, preferably by means of a valve, which is not shown in the Figures.

Alternatively, bypass can occur by means of dialyzer connections 36 and 37, which are connected to a bypass conduit 38 by means of connections 39 and 40. This bypass arrangement is principally designed according to U.S. Pat. No. 4,122,010, which is incorporated herein by reference thereto, and with a pressure monitoring device 41, which detects if a positive or negative pressure arises in conduit 38. If such is the case, and only then, sterilizing and/or cleansing can then take place.

In the example shown in the Figures, a return conduit 42, with a valve 43, extends from the bypass arrangement 38 back to the heating vessel 2. A quantity of the fluid flow recirculates through conduit 42 when the system is to be disinfected and/or sterilized and/or cleansed in any other manner. The remainder of the flow is led from conduit 36, which is connected to connector 39 by means of conduit 38 and connector 40, to the conduit 37, and from there through the ultra-filtration control 23, and then to the outlet 32. A smaller quantity, however, is led directly from the conduit 36 by means of conduit 34, containing valve 35, directly to the conduit 37 for cleansing of the bypass connection.

According to the present invention, a cartridge or other vessel containing a cleansing concentrate is connected at a location designated by reference numerals 1', 1" or 1"' in FIG. 1. An example of such connection is shown in FIG. 2. The cartridge in this case consists of a closed vessel 10f, which is provided at its ends with penetrable membranes 62 and 64.

The cartridge 10f, and means for connecting it to the system according to the present invention, can be designed in accordance with the above-mentioned U.S. Pat. No. 4,784,495. The difference in this case is solely that the cartridge herein contains a cleansing concentrate instead of a treatment concentrate. The cartridge 10f is thus connected to this system with the aid of penetrating nipples 46 and 47, which are arranged on two lever arms, 44 and 45, respectively. Fluid is thus supplied through nipple 46 and removed through nipple 47. The purpose of lever arms 44 and 45 is to permit the system to also be usable without a cartridge. The lever arms are thus swung to a position such that the nipples 46 and 47 are connected instead to a bypass conduit connected to two additional nipples, 48 and 49. These nipples, like the lever arms 44 and 45, are fixed to the wall 60 of a control monitor, which is not shown in FIG. 2, such as the types of control monitors used for controlling dialysis.

Examples of applicable cleansing agents are citric acid, peracetic acid, oxalic acid, sodium hydroxide, sodium hypochloride, sodium carbonates or suitable combinations thereof, although preferably citric acid is employed. When citric acid is used a suitable solution is obtained when 40 grams of citric acid are dissolved in two liters of water, to a concentration of two percent.

Alternatively, the citric acid can be "spiked" with oxalic acid. In this manner, any iron and copper precipitates are dissolved. By way of example, a water solution can be used containing 16 percent citric acid and four percent oxalic acid. This solution provides a very effective cleansing. A further alternative is the use of a water solution comprising 150 g/l of sodium hypochloride, 4 g/l of sodium hydroxide, and 10–25 g/l of sodium carbonate, which also provides an effective cleansing after suitable dilution (to approximately 20 times).

The above-mentioned solutions can be prepared in advance of their intended use. Preferably, however, they are prepared directly in the system, since the connected cartridge contains the concentrates in powdered form.

Many advantages are obtained with the present invention. In addition to the above-mentioned advantages, no mixing of the cleansing solution is therefore required in the clinic or pharmacy. Instead, mixing can take place directly in the system. The possibility of using powder concentrate also offers weight-saving advantages. However, not all concentrates need to be in powder form, since it is important that the invention can also be used with the aid of liquid-based concentrates.

The concentrate cartridges used herein can be connected at the beginning of the cleansing program, and can remain connected during the entire rinsing program, which always follows cleansing. This also makes handling simpler. Cleansing agents which are harmless for the patient can be used. For example, citric acid is a basic foodstuff and, as such, any small remnants are harmless to the patient. Another important advantage is the possibility of using various cleansing agents which are suited to respective treatment systems and conditions of use. The principal function of the system itself is also rendered safer through effective cleansing. For dialysis, the necessary program change in existing programs is very slight.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. Apparatus for controlling the flow of a treatment fluid through a medical treatment device which subjects said treatment fluid to contamination, said apparatus comprising a fluid flow inlet path for feeding said treatment fluid to said medical treatment device, a fluid flow outflow path for withdrawing said contaminated fluid from said medical treatment device, diversion means for diverting a fluid flowing in said fluid flow inlet path from a point in said fluid flow inlet path upstream of said medical treatment device so as to bypass said medical treatment device, and cleaning means for providing a cleaning fluid in place of said treatment fluid for cleaning said apparatus, said cleaning means comprising solvent supply means, cartridge means containing a cleaning composition, and connection means for connecting said cartridge means to said solvent supply means and to said fluid flow inlet path whereby said solvent can be mixed with said cleaning composition in said cartridge means and said mixture can be passed through said fluid flow inlet path so as to clean said fluid flow inlet path when said diversion means diverts said fluid past said medical treatment device.

2. The apparatus of claim 1 including heating means for controlling the supply of heat to said fluid at a predetermined heating location in said fluid flow inlet path.

3. The apparatus of claim 1 wherein said cleaning composition comprises a powder.

4. The apparatus of claim 1 wherein said cleaning composition comprises a liquid concentrate.

5. The apparatus of claim 1 wherein said solvent comprises water.

6. The apparatus of claim 1 wherein said diversion means includes recirculation means for recirculating at least a portion of said fluid from said point in said fluid flow inlet path upstream of said medical treatment device to a point further upstream in said fluid flow inlet path.

7. The apparatus of claim 6 wherein said recirculation means is adapted to recirculate the entire amount of said fluid from said point in said fluid flow inlet path upstream of said medical treatment device to said point further upstream in said fluid flow inlet path.

8. The apparatus of claim 6 including heating means for controlling the supply of heat to said fluid at a predetermined heating location in said fluid flow inlet path, said heating means adapted to increase the temperature of said fluid to a predetermined temperature, whereby the temperature of said fluid in said recirculation means does not drop substantially below said predetermined temperature, and the temperature of said fluid in said fluid flow outflow path is permitted to decrease to a temperature below said predetermined temperature.

9. The apparatus of claim 8 wherein said predetermined temperature is about 90° C., and said temperature below said predetermined temperature is about 80° C.

10. The apparatus of claim 1 including pressure control means for monitoring the pressure in said apparatus whereby said cleaning means can clean said fluid flow inlet path substantially at atmospheric pressure.

11. The apparatus of claim 6 wherein said diversion means includes bypass means for bypassing at least a portion of said fluid from said point in said fluid flow inlet path upstream of said medical treatment device to said fluid flow outflow path.

12. The apparatus of claim 11 wherein said recirculation means is adapted to recirculate a substantial flow of said fluid and wherein said bypass means is adapted to bypass a reduced flow of said fluid, said reduced flow corresponding to only a portion of said substantial flow.

13. The apparatus of claim 6 wherein said recirculation means includes throttle means.

14. The apparatus of claim 13 including throttle control means for opening or bypassing said throttle means during said cleaning, so as to reduce the flow resistance in said fluid flow inlet path.

15. The apparatus of claim 1 wherein said cartridge means comprises a plurality of cartridge means.

16. The apparatus of claim 1 wherein said cartridge means contains a predetermined amount of said cleaning composition, said predetermined amount corresponding to the volume of said treatment fluid normally handled by said apparatus at said cleaning temperature.

17. The apparatus of claim 16 wherein said cartridge means comprises sealed cartridge means and includes an inlet and an outlet, and including penetrable membrane means sealing said inlet and said outlet.

18. The apparatus of claim 16 wherein said cartridge means contains a cleaning composition selected from the group consisting of citric acid, peracetic acid, oxalic acid, sodium hydroxide, sodium hypochloride, sodium carbonate and combinations thereof.

19. The apparatus of claim 18 wherein said cleaning composition comprises citric acid.

20. The apparatus of claim 3 wherein said powder comprises citric acid in crystalline form.

21. A method for controlling the flow of a treatment fluid through a medical treatment device which subjects said treatment fluid to contamination, said method comprising feeding said treatment fluid through a fluid flow inlet path to said medical treatment device, withdrawing said contaminated fluid through a fluid flow outflow path from said medical treatment device, diverting a fluid flowing in said fluid flow inlet path from a point upstream of said medical treatment device through a diversion path so as to bypass said medical treatment device, providing a cleaning fluid in place of said treatment fluid for cleaning said fluid flow inlet path and said diversion path by providing a solvent, connecting a cartridge containing a cleaning composition to said solvent and said fluid flow inlet path, whereby said solvent is mixed with said cleaning composition in said cartridge, and passing said mixture through said fluid flow inlet path ,so as to clean said fluid flow inlet path when said cleaning fluid is diverted through said diversion path.

22. The method of claim 21 including controlling the supply of heat to said fluid at a predetermined heating location in said fluid flow inlet path.

23. The method of claim 21 wherein said cleaning composition comprises a powder.

24. The method of claim 21 wherein said cleaning composition comprises a liquid concentrate.

25. The method of claim 21 wherein said solvent comprises water.

26. The method of claim 21 including recirculating at least a portion of said fluid from said point in said fluid flow inlet path upstream of said medical treatment device to a point further upstream in said fluid flow inlet path.

27. The method of claim 26 including recirculating the entire amount of said fluid from said point in said fluid flow inlet path upstream of said medical treatment device to said point further upstream in said fluid flow inlet path.

28. The method of claim 22 including increasing the temperature of said fluid to a predetermined temperature whereby the temperature of said recirculating fluid does not drop substantially below said predetermined temperature, and the temperature of said fluid in said fluid flow outflow path is permitted to decrease to a temperature below said predetermined temperature.

29. The method of claim 28 wherein said predetermined temperature is about 90° C., and said temperature below said predetermined temperature is about 80° C.

30. The method of claim 21 including monitoring the pressure such that the pressure in said fluid flow inlet path remains substantially at atmospheric pressure.

31. The method of claim 26 including bypassing at least a portion of said fluid from said point in said fluid flow inlet path upstream of said medical treatment device to said fluid flow outflow path.

32. The method of claim 31 including recirculating a substantial flow of said fluid and bypassing a portion of said substantial flow of said fluid.

33. The method of claim 26 including throttling the flow of said fluid during said recirculating.

34. The method of claim 33 including reducing the flow resistance in said fluid flow inlet path during said recirculating.

35. The method of claim 21 including connecting a plurality of said cartridges to said fluid flow inlet path.

36. The method of claim 21 including maintaining said cleaning composition in said cartridge in a predetermined amount corresponding to the volume of said treatment fluid normally carried by said fluid flow inlet path and said temperature of said cleaning fluid.

37. The method of claim 36 including sealing said cartridge by means of permeable membranes.

38. The method of claim 36 wherein said cleaning composition is selected from the group consisting of citric acid, peracetic acid, oxalic acid, sodium hydroxide, sodium hypochloride, sodium carbonate and mixtures thereof.

39. The method of claim 38 wherein said cleaning composition comprises citric acid.

40. The method of claim 23 wherein said powder comprises crystalline citric acid.

* * * * *